United States Patent [19]

Lafon

[11] 4,066,686

[45] Jan. 3, 1978

[54] NEW BENZHYDRYSULPHINYL DERIVATIVES

[75] Inventor: Louis Lafon, Paris, France

[73] Assignee: Laboratoire L. Lafon, Maisons Alfort, France

[21] Appl. No.: 728,054

[22] Filed: Sept. 30, 1976

[30] Foreign Application Priority Data

Oct. 2, 1975 United Kingdom ............... 40419/75

[51] Int. Cl.$^2$ ..................... C07C 83/10; A61K 31/185
[52] U.S. Cl. ............................. 260/500.5 H; 560/11; 260/239 BF; 260/268 BZ; 260/293.73; 260/326.82; 260/465 R; 260/516; 260/564 R; 260/564 G; 260/570.5 S; 260/609 D; 424/244; 424/248.5; 424/250; 424/267; 424/315; 424/325; 424/326; 544/158; 548/342
[58] Field of Search ................................. 260/500.5 H

[56] References Cited

U.S. PATENT DOCUMENTS

| | | | |
|---|---|---|---|
| 2,394,597 | 2/1946 | Dickey et al. | 260/500.5 H |
| 3,479,396 | 11/1969 | Buu-Hoi et al. | 260/500.5 H |

OTHER PUBLICATIONS

Zayed et al, "Archiv der Pharmazie" No. 6 (1967) pp. 526 to 533.

Primary Examiner—Joseph E. Evans
Attorney, Agent, or Firm—Poms, Smith, Lande & Glenny

[57] ABSTRACT

The invention provides the benzhydrylsulphinyl derivatives of the formula:

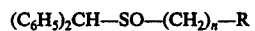

$$(C_6H_5)_2CH-SO-(CH_2)_n-R \qquad I$$

where $n$ is 1, 2 or 3 and R is $C(=O)NHOH$, $C(=NH)NH_2$, $C(=NH)NHOH$, 2-$\Delta^2$-imidazolinyl or $NR_1R_2$ (where $R_1$ is H or $C_1$-$C_3$-alkyl and $R_2$ is H, $C_1$-$C_3$-alkyl, or $CH_2CH_2OH$, and $R_1$ and $R_2$ considered together can form, with the nitrogen atom to which they are bonded, a N-heterocyclic group of 5 to 7 ring members, which can be substituted and can contain a second hetero-atom such as O and N), and their addition salts. These products are useful in therapy for treating disturbances of the central nervous system.

4 Claims, No Drawings

NEW BENZHYDRYSULPHINYL DERIVATIVES

The present invention relates to benzhydrylsulphinyl derivatives, to their preparation, and their use in therapy.

The invention provides, as new compounds, the benzhydrylsulphinyl derivatives of the general formula

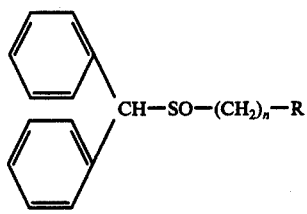

I in which $n$ is 1, 2 or 3 and R is C(=O)—NHOH, C(=NH)—NH$_2$, C(=NH)—NHOH, 2-$\Delta^2$-imidazolinyl, or NR$_1$R$_2$, where R$_1$ is hydrogen or C$_1$-C$_3$ alkyl, R$_2$ is hydrogen, C$_1$-C$_3$ alkyl or CH$_2$-CH$_2$OH, or R$_1$ and R$_2$ together with the nitrogen atom to which they are bonded form a N-heterocyclic group of 5 to 7 ring members which can contain a second heteroatom such as O and N and can be substituted, and their addition salts. By addition salts are meant their addition salts with acids and their quaternary ammonium salts.

The N-heterocyclic group NR$_1$R$_2$ can be, in particular, morpholino, piperidino, pyrrolidino, 4-methyl-piperazino, 4-(4-chlorophenyl)-piperazino, 4-methyl-piperidino or azepino. The preferred groups are morpholino and piperidino.

According to the invention, the products of formula I are prepared by oxidizing a sulphide of the formula

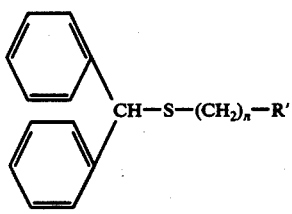

II where $n$ is as defined above and R' is the same as R or is a radical convertible thereto, with H$_2$O$_2$, preferably in an acetic acid medium. The oxidation may be carried out in acetic acid using concentrated hydrogen peroxide, i.e. hydrogen peroxide of at least 110 volumes strength (that is to say water containing at least 33% by weight of hydrogen peroxide). During this oxidation, it is necessary to avoid the formation of a relatively large amount of the corresponding sulphonyl derivative. In practice, if the reaction is carried out at 100° C for 1 hour or more, with hydrogen peroxide of 110-124 volumes strength, essentially only the said sulphonyl derivative is obtained; thus, in order only to obtain the sulphinyl derivative, the reaction is carried out at a temperature less than or equal to 50° C (in general over the course of 1 hour or more). As the reaction is exothermic, a temperature of 37° to 45° C is arrived at by simply mixing the reactants in acetic acid, without additional heating.

It is possible to form first a benzhydrylsulphinyl compound of the formula IV, where R' is a precursor of the nitrogen-containing group R (especially a cyano group, an amino-forming group, a carboxylic acid group or a carboxylate group) and then subsequently to form or introduce the group R, in accordance with the following reaction scheme:

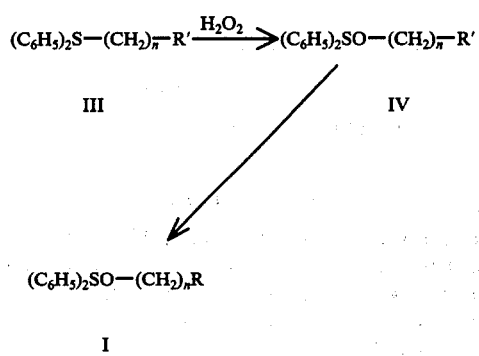

The reactions involved are all known in themselves.

Example 1 bis below describes operating conditions for obtaining a compound by this method on an industrial scale.

It is preferred to use approximately stoichiometric amounts of hydrogen peroxide and of the sulphide of formula II.

These examples below illustrate the methods of obtaining the sulphides used as starting materials, and the preparation of the addition salts from the bases of the formula I (for example, by reacting the free base with an inorganic or organic acid). Amongst the acids which can be used, there may especially be mentioned hydrochloric, hydrobromic, hydriodic, sulphuric, formic, maleic, fumaric, oxalic, ascorbic, citric, acetic, methanesulphonic, p-toluenesulphonic, lactic, succinic, benzoic, salicylic, acetylsalicylic, malic, tartaric, glutamic and aspartic acid.

According to the invention, a therapeutic composition is proposed which is characterised in that it contains at least one compound of the formula I, or one of its possible non-toxic addition salts, in association with a physiologically acceptable excipient.

Table I below lists a certain number of products according to the invention which have been synthesised.

TABLE I (C$_6$H$_5$)$_2$CH—SO—(CH$_2$)$_n$—R

| Example | Code No. | n | R | Melting point, ° C |
|---|---|---|---|---|
| 1 | CRL 40,028 | 1 | C(=O)NHOH | 159–160 |
| 2(a) | CRL 40,048 | 1 | C(=NH)NHOH | 150 (decomposition) |
| 3(a) | CRL 40,066 | 2 | 2-$\Delta^2$-imidazolinyl | 162–164 |
| 4(a) | CRL 40,221 | 2 | morpholino | 166–168 |
| 5(a) | CRL 40,222 | 2 | piperidino | 206–210 (decomposition) |
| 6 | CRL 40,260 | 2 | C(=O)NHOH | 159–160 |
| 7(a) | CRL 40,261 | 2 | C(=NH)NHOH | 164–166 |
| 8(a) | CRL 40,277 | 3 | C(=NH)NHOH | 200–204 (decomposition) |
| 9 | CRL 40,278 | 3 | C(=O)NHOH | 143 |

Note: (a)hydrochloride

Other advantages and characteristics will be more readily understood on reading the preparation examples given below, which do not imply any limitation and are given by way of illustration. The melting points were determined on a Köfler bench.

EXAMPLE 1

Benzhydrylsulphinyl-acetohydroxamic Acid

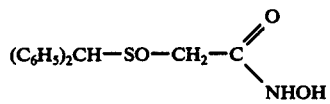

Code No. CRL 40,028 a. Diphenylmethane-thiol 15.2 g (0.2 mol) of thiourea and 150 ml of demineralised water are introduced into a 500 ml three-neck flask equipped with a central mechanical stirrer, and with a dropping funnel and a condenser on the (respective) side-necks.

The temperature of the reaction mixture is brought to 50° and 49.4 g (0.2 mol) of bromodiphenylmethane are added all at once whilst continuing the heating.

After refluxing for about 5 minutes, the solution, which has become limpid, is cooled to 20° C and 200 ml of 2.5 N NaOH are then added dropwise whilst maintaining the said temperature.

The temperature is then again kept at the reflux for 30 minutes after which, when the mixture has returned to ordinary temperature (15°–25° C), the aqueous solution is acidified with 45 ml of concentrated hydrochloric acid. The supernatant oil is extracted with 250 ml of diethyl ether and the organic phase is washed with 4 × 80 ml of water and then dried over magnesium sulphate. 39 g of crude diphenylmethane-thiol are thus obtained. Yield = 97.5%.

b. Benzhydryl-thioacetic acid 10 g (0.05 mol) of diphenylmethane-thiol and 2 g (0.05 mol) of NaOH dissolved in 60 ml of demineralised water are introduced successively into a 250 ml flask equipped with a magnetic stirrer and a reflux condenser. The reactants are left in contact for 10 minutes whilst stirring, and a solution consisting of 7 g (0.075 mol) of chloroacetic acid, 3 g (0.075 mol) of NaOH pellets and 60 ml of demineralised water is then added all at once.

The aqueous solution is gently warmed to about 50° C for 15 minutes, washed with 50 ml of ether, decanted and acidified with concentrated hydrochloric acid. After filtration, 10.2 g of benzhydryl-thioacetic acid are thus obtained. Melting point 129°–130° C. Yield = 79%.

c. Ethyl benzhydryl-thioacetate

The following reaction mixture is heated under reflux for 7 hours: 10.2 g (0.0395 mol) of benzhydryl-thioacetic acid, 100 ml of anhydrous ethanol and 2 ml of sulphuric acid.

When heating has been completed, the ethanol is evaporated in vacuo; the oily residue is taken up in 100 ml of ethyl ether and the organic solution is then washed with water, with an aqueous sodium carbonate solution and then with water until the wash waters have a neutral pH. After drying over sodium sulphate, the solvent is evaporated. 10.5 g of ethyl benzhydryl-thioacetate are thus obtained. Yield = 93%.

d. Benzhydryl-thioacetohydroxamic acid

The following three solutions are prepared:

| 1. | Ethyl benzhydryl-thioacetate | 10.8 g (0.0378 mol) |
| | Methanol | 40 ml |
| 2. | Hydroxylamine hydrochloride | 5.25 g (0.0756 mol) |
| | Methanol | 40 ml |
| 3. | Potassium hydroxide pellets | 7.5 g (0.0134 mol) |
| | Methanol | 40 ml |

The solutions are heated, if necessary, until they become limpid, and when the temperatures have again fallen to below 40° C, the solution of potassium hydroxide in methanol is poured into the solution of hydroxylamine hydrochloride in alcohol. Finally, at a temperature of about 5° to 10° C, the solution of ethyl benzhydryl-thioacetate is added in its turn. After leaving the reactants in contact for 10 minutes, the sodium chloride is filtered off and the limpid solution obtained is kept for about 15 hours at ordinary temperature. The methanol is then evaporated under reduced pressure, the residual oil is taken up in 100 ml of water and the aqueous solution is acidified with 3 N hydrochloric acid. The hydroxamic acid which has crystallised is filtered off, washed with water and then dried. 9.1 g of product are obtained. Yield = 87.5%. Melting point 118°–120° C.

e. CRL 40,028

10.4 g (0.038 mol) of benzhydryl-thioacetohydroxamic acid are oxidised at 40° C, over the course of 2 hours, by means of 3.8 ml (0.038 mol) of hydrogen peroxide of 110 volumes strength, in 100 ml of acetic acid.

When the oxidation has ended, the acetic acid is evaporated under reduced pressure and the residual oil is taken up in 60 ml of ethyl acetate. The product which has crystallised is filtered off and then purified by recrystallisation from a 3:2 (by volume) mixture of ethyl acetate and isopropyl alcohol.

8 g of CRL 40,028 are thus obtained. Melting point 159°–160° C. Yield = 73%.

Solubility in water <1 g/l.

Example 1 Bis

Example 1 bis relates to the working procedure for the manufacture of benzhydrylsulphinyl-acetohydroxamic acid, the subject of Example 1 above, on an industrial scale.

a. Synthesis of benzhydryl-thioacetic acid 1.003 kg of thiourea are dissolved in 5.72 liters of 48% strength hydrobromic acid and 0.880 liter of water in a 20 liter reactor. The mixture is heated to 60° and 2.024 kg of benzhydrol are introduced. The temperature is raised to 95° C and the mixture is then allowed to cool to ambient temperature, 15°–25° C. The crystals are filtered off and washed with water. They are then again worked into a paste in 5.5 liters of water, and introduced into a 20 liter reactor, together with 3.5 liters of sodium hydroxide solution ($d = 1.33$). The mixture is heated to 70° C and 1,144 g of chloroacetic acid dissolved in 2.2 liters of water are run in slowly. Reflux is maintained for 30 minutes after running in the chloroacetic acid. The mixture is then allowed to cool to ambient temperature (thus giving benzhydryl-thioacetic acid, which is not isolated).

b. Synthesis of benzhydrylsulphinylacetic acid 1,430 liters of hydrogen peroxide of 130 volumes strength are run, in the course of 3 hours, into the preceding reaction mixture, at about 30° C. Thereafter, the batch is run into 22 liters of water, the insoluble material is filtered off and the filtrate is then acidified with hydrochloric acid ($d = 1.18$). The product is filtered off, washed with water by again working it into a paste (with water), and suction-drained. Benzhydrylsulphinylacetic acid is thus obtained.

c. Synthesis of methyl benzhydrylsulphinylacetate

The preceding acid is introduced into a 20 liter reactor with 6 liters of water. 1.1 liters of sodium hydroxide solution ($d = 1.33$) and 1.848 kg of sodium bicarbonate are added. 2.1 liters of dimethyl sulphate are then added. After 1 hour, the crystallisation is started. The product is filtered off, suction-drained and washed. Methyl benzhydrylsulphinylacetate is obtained.

d. Synthesis of benzhydrylsulphinylacetohydroxamic acid (CRL 40,028)

8.3 liters of water, 3.3 liters of sodium hydroxide solution ($d = 1.33$) and 1.529 kg of hydroxylamine hydrochloride are introduced into a 20 liter reactor.

The preceding ester is then added and the mixture is stirred for 4 hours. This solution is poured into a mixture of 17 liters of water, 3 liters of hydrochloric acid ($d = 1.18$) and 4 liters of methylene chloride, and the whole is stirred. The crystals are filtered off and again worked into a paste in 9 liters of water and then in 5 liters of methylene chloride. The crystals are dried to constant weight in a vacuum over at 30° C. The product is recrystallised from chloroform. Pure benzhydrylsulphinylacetohydroxamic acid is obtained in an overall yield of 53%.

Melting point = 158–160° C.

EXAMPLE 2

Benzhydrylsulphinylacetamidoxime hydrochloride

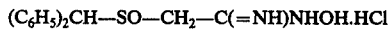

Code No. CRL 40,048 a. Benzhydryl-thioacetonitrile 20 g (0.1 mol) of diphenylmethane-thiol, 50 ml of anhydrous ethanol and 100 ml (0.1 mol) of 1 N sodium hydroxide solution are introduced into a 250 ml flask equipped with a magnetic stirrer.

After 15 minutes contact at ordinary temperature, 6.91 ml (0.11 mol) of chloroacetonitrile are added dropwise and the reactants are then again left in contact for 30 minutes. When the reaction has ended, the ethanol is evaporated under reduced pressure and the water-insoluble nitrile is then extracted with 150 ml of ethyl acetate; the organic phase is washed with 3 times 50 ml of water and dried over magnesium sulphate. After evaporating the solvent, the residual oil, taken up in the minimum amount of isopropanol, allows 13.3 g of benzhydryl-thioacetonitrile to separate out. Melting point = 77°–78° C. Yield 55.6%.

b. Benzhydryl-thioacetamidoxime hydrochloride 11 g (0.11 mol) of potassium bicarbonate, 7.65 g (0.11 mol) of hydroxylamine hydrochloride and 50 ml of demineralised water are introduced into a 250 ml single-neck flask equipped with a magnetic stirrer and a condenser.

When the effervescence caused by the evolution of $CO_2$ has ceased, 13.3 g (0.0556 mol) of benzhydryl-thioacetonitrile dissolved in 200 ml of butanol are added all at once and the temperature of the reaction mixture is then brought to the reflux temperature of the water-butanol azeotrope over the course of 3 hours. When the reaction has ended, the solvents are evaporated under reduced pressure, the residual oil is taken up in 150 ml of ethyl acetate, and the organic solution is washed with twice 50 ml of water and is then dried over magnesium sulphate. After filtering off the $MgSO_4$, the amidoxime hydrochloride is precipitated by adding a solution of hydrogen chloride in ether. 15.3 g of benzhydryl-thioacetamidoxime hydrochloride are thus obtained, of which the base, liberated by ammonia, melts at 112° C. Yield = 89%.

c. CRL 40,048

15.4 g (0.05 mol) of benzhydryl-thioacetamidoxime hydrochloride are oxidised for 1 hour at 45° C with 5 ml (0.05 mol) of hydrogen peroxide of 110 volumes strength in 120 ml of pure glacial acetic acid. When the oxidation has ended, the acetic acid is evaporated under reduced pressure and the residual oil, taken up in 300 ml of demineralised water, is rendered alkaline with ammonia after having filtered the aqueous solution through animal charcoal. The crystalline amidoxime base, melting at 143° C, is filtered off, dried and then taken up in 100 ml of acetone; the hydrochloride is precipitated by adding a solution of hydrogen chloride in ether; 11.5 g of CRL 40,048, which decomposes from 150° C onwards, are thus obtained. Yield = 71%. Determination of inorganic chlorine (Volhard method):

Calculated: 10.92%. Found: 11.17%.
solubility in water: 100 g/l.

EXAMPLE 3

2-(2-Benzhydrylsulphinyl-ethyl)-Δ²-imidazoline hydrochloride

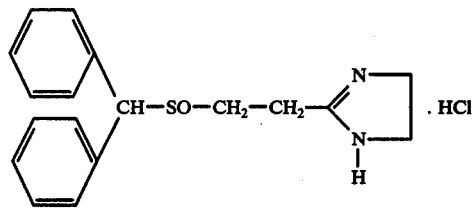

Code No. CRL 40,066 a. Hydrochloride of benzhydryl-thiopropioniminoethyl ester 9.2 ml (0.2 mol) of 3-chloropropionitrile are added, in the cold, to a (stirred) solution of 20 g (0.1 mol) of benzhydryl-thiol in 75 ml of ethanol and 110 ml of 1 N NaOH. The mixture is stirred for 1 hour at 30° C and then extracted with ether, and the extract is washed with water, dried and filtered. 10 ml of ethanol are added to the filtrate and the mixture is saturated with dry HCl gas; the reactants are left in contact for 48 hours. 100 ml of ether are added and the mixture is filtered to give 23 g of product. Melting point = 70°–75° C.

b. 2-(2-Benzhydryl-thioethyl)-Δ²-imidazoline hydrochloride

A solution of 15.5 g (0.046 mol) of the hydrochloride of the preceding iminoester and 3.5 ml of ethylenediamine in 100 ml of ethanol is heated under reflux for 2 hours. It is evaporated to dryness in vacuo, taken up in water with 1 to 2 drops of concentrated HCl, and extracted with ether. The base is precipitated with concentrated NaOH, filtered off and washed with water.

11 g of product are obtained. Yield = 81%. Melting point: 102°-103° C.

c. CRL 40,066

11.6 g (0.035 mol) of 2-(2-benzhydryl-thioethyl)-Δ²-imidazoline hydrochloride dissolved in 35 ml of acetic acid are oxidised with 3.5 ml of hydrogen peroxide of 110 volumes strength over the course of 1 hour at 50° C. The mixture is evaporated to dryness in vacuo, and the residue is taken up in acetone and filtered off. The product is recrystallised from isopropanol. CRL 40,066 is obtained in an overall yield of 40%. It is a white powder melting, with decomposition, at 162°-164° C.

EXAMPLE 4

N-[2-(Benzhydrylsulphinyl)-ethyl]-morpholine hydrochloride

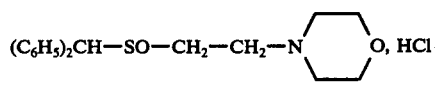

Code No. CRL 40,221 a. N-[2-(Benzhydryl-thio)-ethyl]-morpholine hydrochloride 7.6 g (0.1 mol) of thiourea and 100 ml of demineralised water are introduced into a 500 ml three-neck flask equipped with a magnetic stirrer, a dropping funnel and a condenser; the mixture is heated to 50° C and 20.25 g (18 ml; 0.1 mol) of chlorodiphenylmethane are then added all at once. The solution is left refluxing until it has become limpid, and is then cooled to 20° C, and 200 ml of 2.5 N NaOH are added dropwise.

The resulting solution (which contains the sodium benzhydrylthiolate thus formed) is then kept under reflux for 1 hour; after it has returned to 50° C, a solution of 18.6 g (0.1 mol) of 2-chloroethyl-morpholine hydrochloride in 80 ml of water is added dropwise. The temperature of the reaction mixture is then brought to the reflux point over the course of 2 hours.

The mixture is cooled, the oil formed is extracted with ether and the ether solution is then extracted with 3 times 70 ml of N HCl. The expected product precipitates from water in an acid medium. It is filtered off and then recrystallised from isopropanol. 26.6 g of N-[2-(benzhydryl-thio)-ethyl]-morpholine hydrochloride are thus obtained.

Melting point 176° C. Yield relative to chlorodiphenylmethane: 76%.

b. CRL 40,221

24.8 g (0.0711 mol) of the hydrochloride obtained above, dissolved in 70 ml of pure acetic acid, are oxidised with 6.4 ml of hydrogen peroxide of 125 volumes strength. The reaction is carried out at 40° C over the course of 1 hour 30 minutes. The acetic acid is then evaporated in vacuo and the residual oil is taken up in ether, from which CRL 40,221 crystallises on addition of acetone. 18.9 g of product are thus obtained. Melting point = 166°-168° C. Overall yield = 52%.

Chlorine determination (Volhard method): Theoretical; 9.7%, Determined; 9.7%.

EXAMPLE 5

N-[2-(Benzhydrylsulphinyl)-ethyl]-piperidine hydrochloride

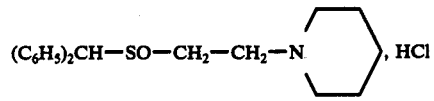

Code No. CRL 40,222.

The procedure indicated in Example 4 is followed. N-[2-(Benzhydryl-thio)-ethyl]-piperidine hydrochloride (melting point = 174°-176° C) is thus obtained. Oxidation of this sulphide with $H_2O_2$ gives CRL 40,222. Melting point = 206°-210° C (with decomposition). Overall yield: about 50%.

Chlorine determination (Volhard method); Theory; 9.75%, Found; 9.8%.

EXAMPLE 6

3-(Benzhydrylsulphinyl)-propionohydroxamic acid

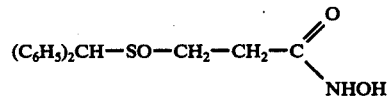

Code No. CRL 40,260 a. Methyl 3-(benzhydrylthio)-propionate

A solution of 0.1 mol of sodium benzhydryl-thiolate is prepared in a strongly alkaline medium (prepared as indicated in Example 4a). A solution of 0.15 mol of sodium 3-chloropropionate [obtained by dissolving 0.15 mol (16.3 g) of 3-chloropropionic acid and 0.075 mol (7.6 g) of $Na_2CO_3$ in water] is added to the above solution at about 60° C. Thereafter the temperature is raised to the boil, the mixture is left under reflux for about half an hour and is then cooled, filtered over charcoal and acidified with concentrated HCl, and 16.0 g of 3-(benzhydryl-thio)-propionic acid are thus precipitated. Melting point = 88°-90° C.

Yield relative to chlorodiphenylmethane = 59%.

The corresponding methyl ester is then prepared by dissolving 16 g (0.059 mol) of the preceding acid in 40 ml of 1,2-dichloroethane to which 10 ml of methanol and 0.1 ml of concentrated $H_2SO_4$ have been added. The whole is heated to the reflux temperature for about 5 hours, cooled, and decanted, the aqueous phase is discarded and the organic phase is washed with a saturated sodium bicarbonate solution and then with water until the wash waters have a neutral pH. After drying over $MgSO_4$ and evaporating the solvent, 15.7 g (0.055 mol) of the ester (a limpid yellow oil) are obtained. Yield relative to the acid: 93%. Yield relative to chlorodiphenylmethane = 55%.

b. 3-(Benzhydryl-thio)-propionohydroxamic acid 0.055 mol (15.7 g) of the preceding ester, dissolved in 50 ml of methanol, is added to a solution of 0.15 mol of hydroxylamine base [prepared by neutralising 0.15 mol (10.4 g) of hydroxylamine hydrochloride with 0.15 mol of sodium methylate]. The whole is left at ordinary temperature (15°–25° C) for 48 hours, the sodium chloride is filtered off, the methanol is evaporated, the residue is taken up with aqueous alkali, the solution is filtered over charcoal, the filtrate is acidified with concentrated HCl, and the desired hydroxamic acid (8.3 g) is thus obtained. It is recrystallised from benzene and 7.6 g of pure hydroxamic acid are isolated. Melting point: 106°–108° C. Yield relative to the ester: 48%.

c. CRL 40,260

0.0264 mol (7.6 g) of the preceding hydroxamic acid, dissolved in 27 ml of anhydrous $CH_3$—COOH, is reacted with 2.4 ml of $H_2O_2$ of 124 volumes strength. The mixture is left at 40°–45° C for 1½ hours, the acetic acid is evaporated and the residue is taken up in 50 ml of ethyl acetate; the CRL 40,260 crystallises. It is recrystallised from isopropanol and 7.1 g are thus obtained. Melting point = 159°–160° C. Yield from the oxidation: 88%. Overall yield 23.5%.

EXAMPLE 7

3-(Benzhydrylsulphinyl)-propionamidoxime hydrochloride Code No. CRL 40,261 a. 3-(Benzhydrylthio)-propionitrile

A solution of 0.1 mol of sodium benzhydryl-thiolate (compare Example 4a) is prepared and 9 ml(0.115 mol) of β-chloropropionitrile are then added at 60°–70° C. The mixture is thereafter heated for half an hour under reflux and is cooled, the oil is extracted with ether and the ether solution is washed with water and dried. After evaporating the solvent, 24.5 g of nitrile (a limpid green oil) are obtained. Yield: 97%.

b. 3-(Benzhydryl-thio)-propionamidoxime hydrochloride 24.5 g of the preceding nitrile are dissolved in about 100 ml of 1-butanol. A solution of 0.25 mol of hydroxylamine base in 50 ml of water [obtained by neutralising 17.4 g of hydroxylamine hydrochloride with 21 g of sodium bicarbonate] is added to the preceding solution. The whole is heated at the reflux temperature of the butanol-water (2:1) azeotrope, whilst maintaining vigorous stirring, for at least 4 hours. It is then cooled, the butanol is evaporated and the residue is taken up with water under neutral conditions 3-(benzhydryl-thio)-propionamidoxime precipitates. 19.1 g of the base (a white powder which is soluble in alcohols, melting point = 106°–108° C) are thus obtained. The corresponding hydrochloride is prepared by adding HCl to a suspension of the base in water until the pH is acid; the hydrochloride, which is soluble in the hot medium, crystallises on cooling the acid solution. 18.4 g of 3-(benzhydrylthio)-propionamidoxime hydrochloride are thus obtained. Melting point: 186°–188° C. Overall yield 57%.

c. CRL 40,261

18.4 g (0.057 mol) of the preceding hydrochloride, dissolved in 60 ml of $CH_3$—COOH, are reacted with 5.2 ml of $H_2O_2$ of 124 volumes strength, at 40°–45° C, for about 1 hour 30 minutes. The acetic acid is evaporated and the residue is taken up in ethyl acetate; CRL 40,261 crystallises. It is recrystallised from water and 17.3 g of product are isolated. Melting point 164°–166° C. Overall yield: 51%.

EXAMPLE 8

4-(Benzhydrylsulphinyl)-butyramidoxime hydrochloride Code No. CRL 40,277

Using the procedure indicated in Example 7, the following are obtained successively:

4-(benzhydryl-thio)-butyronitrile, which is in the form of a limpid oil, 4-(benzhydryl-thio)-butyramidoxime (melting point = 78°–80° C), the corresponding hydrochloride (melting point = 132°–133° C) and CRL 40,277, melting point = 200°–204° C (with decomposition).

EXAMPLE 9

4-(Benzhydrylsulphinyl)-butyrohydroxamic acid Code No. CRL 40,278.

Using the procedure described in Example 6, the following are obtained successively:

4-(benzhydryl-thio)-butyric acid (melting point = 91°–92° C), ethyl 4-(benzhydryl-thio)-butyrate (which is in the form of an oil), 4-(benzhydryl-thio)-butyrohydroxamic acid (melting point 110° C) and CRL 40,278, melting point = 143° C.

The results of the pharmacological tests which were carried out have been summarised below. These experiments show that the products of the formula I act on the central nervous system.

A. Experiments relating to CR1 40,028 (Example 1)

Toxicity

The LD 50 in mice, for gastric administration, is 1,950 mg/kg. For intraperitoneal administration, in mice, no mortality was observed at doses of 256 mg/kg, 512 mg/kg and 1,024 mg/kg; the LD 50 for intraperitoneal administration, in mice, appears to be less than or equal to 2,048 mg/kg.

The fact that the LD 50 for gastric administration is close to the LD 50 for intraperitoneal administration suggests that the product overcomes the intestinal barrier readily, all the more so since at all the doses studied, excitation of the animal was observed.

Interaction with apomorphine

Batches of 6 rats are given CRL 40,028 30 minutes after the subcutaneous injection of 0.5 mg/kg of apomorphine. It is found that CRL 40,028 does not exert any activity on the stereotype behaviour caused by apomorphine.

The results obtained in accordance with the method of Table II given later have been shown in Table III.

TABLE III

| | Number of rays crossed in 30 minutes | % relative to the control animals | % variation |
|---|---|---|---|
| Control animals | 200 | 100 | — |
| CRL 40,028 64 mg/kg - 30 mins | 311 | 155 | +55 |
| CRL 40,028 64 mg/kg - 1 hr | 424 | 212 | +112 |
| CRL 40,028 64 mg/kg - 2 hrs | 376 | 188 | +88 |

TABLE III-continued

|  | Number of rays crossed in 30 minutes | % relative to the control animals | % variation |
|---|---|---|---|
| CRL 40,028 64 mg/kg - 4 hrs | 234 | 117 | +17 |

It can be seen from the analysis of Table III that CRL 40,028 brings about a hypermotility which appears in less than 30 minutes, reaches a maximum after one hour and disappears in 4 hours.

Effect on the motility

1. Spontaneous motility

CRL 40,028 increases the motor activity of the animals from a dose of 16 mg/kg onwards. As this effect is representative of the activity of CRl 40,028, attempts have been made to obtain its kinetics more precisely. Batches of 12 mice per dose, and 24 control animals, were given CRL 40,028 at various times, at a dose of 64 mg/kg of the gummy solution, in accordance with the scheme of Table II as regards the administration of the gummy solution and of the product.

2. Residual motility

The stimulating effect of CRL 40,028 is brought more into evidence as the spontaneous motor activity is reduced by the animals becoming accustomed to the chamber.

3. Motor recovery after hypoxia aggression

After anoxia, the mice which have received CRL 40,028 at doses of 512, 128 and 32 mg/kg, exhibit a markedly greater motor activity than that of the control animals.

It follows from the experiments recorded above that CRL 40,028 possesses stimulant properties, namely causing excitation and hyper-reactivity, and hypermotility, in animal psychopharmacology.

In order to establish whether or not CRL 40,028 approaches amphetamine-type agents or psychostimulant agents, comparative experiments were carried out with amphetamine and caffeine, and are reproduced in Table IV.

TABLE IV

| Tests | CRL 40,028 | Amphetamine | Caffeine |
|---|---|---|---|
| Excitation | + | ++ | ++ |
| Reactivities | ↑ | ↑ | ↑ |
| Temperature (S) | ±↓ | ↑ | ↑ |
| Temperature (R) | 0 | ↑ | ±↑ |
| Stereotypies | 0 | + | ± |
| Boosting action on apomorphine | 0 | + | + |
| Boosting action on amphetamine | 0 | | ± |
| Anti-reserpine action (temperature) | ± | + | + |
| Anti-reserpine action (ptosis) | 0 | + | 0 |
| Anti-oxotremorine action (temperature) | ± | + | + |
| Anti-oxotremorine action (trembling) | + | + | 0 |
| Anti-oxotremorine action (peripheral) | 0 | + | 0 |
| Four plate test | ↑ | ↑ | ↑ |
| Convulsions by electric shock | ↓ | ↑ | ↑ |
| Spontaneous motility | | ↑ | ↑ |
| Residual motility | ↑+++ | | ↑+++ |
| Motor recovery after hypoxia | ↑+++ | (a)↑ | (a)↑ |
| Group toxicity | ± | + | 0 |

Note:
(a) mortality

Interaction with amphetamine

Amphetamine (2 mg/kg, given intraperitoneally) is injected 30 minutes after the administration of CRL 40,028 (6 rats/dose). CRL 40,028 does not produce an overall change in the stereotype behaviour induced by amphetamine in rats; it does not boost the action of amphetamine.

Interaction with reserpine

Batches of 6 mice are given an intraperitoneal injection of reserpine (2.5 mg/kg) 4 hours before the administration of CRl 40,028.

1. Effect on the temperature

At 256 and 64 mg/kg CRL 40,028 partially counteracts the hypothermic effect of reserpine.

2. Effect on ptosis

CRL 40,028 does not resolve the palpebral ptosis produced by reserpine.

Interaction with oxotremorine

Mice (6 per dose) are given an intraperitoneal injection of 0.5 mg/kg of oxotremorine 30 minutes after the administration of CRL 40,028.

1. Effect on the temperature

CRL 40,028 at certain doses (256, 16 and 4 mg/kg, but not 64 mg/kg) moderately opposes the hypothermic effect of oxotremorine.

2. Effect on trembling

CRL 40,028 moderately reduces, at all the doses, the intensity of the trembling brought about by oxotremorine.

3. Effect on the peripheral cholinergic symptoms

CRL 40,028 does not alter the increase in salivation, lachrymation and defaecation brought about by oxotremorine.

Effect on the four plate test, traction and electric shock

The test is carried out on batches of 20 mice, 30 minutes after the administration of CRL 40,028.

At high doses (256 and 64 mg/kg) CRL 40,028 produces an increase in the number of passes which entail pain. At a low dose (4.1 mg/kg) it appears to bring about a modest decrease in the number of such passes. At no dose does CRL 40,028 bring about a major decrease in motility. Only at a high dose (256 mg/kg) does it exert a very moderate antagonism against the convulsive effects of the electric shock.

TABLE II

|  | − 4 hrs | − 2 hrs | − 1 hr | − 30 mins | 0 to + 30 mins |
|---|---|---|---|---|---|
| Control animals | Gummy solution | Gummy solution | Gummy solution | Gummy solution | Actimetry |
| CRL 40,028 64 mg/kg - 4 hrs | CRL 40,028 | Gummy solution | Gummy solution | Gummy solution | Actimetry |
| CRL 40,028 64 mg/kg - 2 hrs | Gummy solution | CRL 40,028 | Gummy solution | Gummy solution | Actimetry |
| CRL 40,028 64 mg/kg - 1 hr | Gummy solution | Gummy solution | CRL 40,028 | Gummy solution | Actimetry |

TABLE II-continued

|  | − 4 hrs | − 2 hrs | − 1 hr | − 30 mins | 0 to + 30 mins |
|---|---|---|---|---|---|
| CRL 40,028 64 mg/kg - 30 mins | Gummy solution | Gummy solution | Gummy solution | CRL 40,028 | Actimetry |

It emerges from these comparative tests that CRL 40,028 differs from the amphetamine-type compounds by:
the absence of stereotypies,
the absence of boosting of the effect of apomorphine and of amphetamine,
the absence of a marked antagonism to reserpine, and
the virtual absence of specific (?) toxicity in the groups of mice.

Accordingly, one is dealing with a psychostimulant which comes closer to caffeine, in spite of certain differences, namely:
the absence of boosting of the effect of apomorphine,
the absence of a marked antagonism to hypothermia brought about by reserpine, and
the absence of an aggravation of the effects of electric shock and of hypoxia.

B. Tests on the other products

1. CR1 40,048 (Example 2) acts only on the central nervous system. It has an antagonist action on oxotremorine, in the absence of a mydriatic effect. It boosts stereotypies produced by amphetamine-type compounds and produces hyper-reactivity to the touch in mice.

2. CRL 40,066 (Example 3) exhibits, alongside an effect on the central nervous system, an anti-oedema effect in the carrageenin oedema.

3. CRL 40,221 (Example 4) exhibits a psychopharmacological spectrum close to that of tricyclic anti-depressants, namely
an anti-reserpine effect,
an anti-oxotremorine effect,
a (metabolic) boosting of the stereotypies produced by amphetamine-type compounds,
a protection against convulsions produced by electric shock,
a considerable mydriasis and
hypothermia at high doses.

Furthermore, it exhibits (a) a certain effect in the four plate test (like imipramine and amitriptyline but not nortriptyline) and (b) a sedation at doses close to the toxic dose (like imipramine and nortriptyline, but not amitriptyline). Finally, it produces a resumption of motor activity in mice accustomed to their chamber.

CRL 40,221, administered intraperitoneally in mice exhibits an LD-O greater than 512 mg/kg 4. CRL 40,222 (Example 5) acts on the central nervous system and the following are observed in its psychopharmacological spectrum:
an increase in the duration of the stereotypies brought about by amphetamine,
a moderate action towards oxotremorine,
the absence of an anti-reserpine effect,
an increase in the spontaneous motility in mice (only at a low dose of 1 mg/kg ) and a stimulation of the residual motility in mice (at a dose of 8 mg/kg).

CRL 40,222, administered intraperitoneally in mice, has an LD-O greater than 128 mg/kg.

5. CRL 40,260 (Example 6) is a substance of low toxicity (its LD-O is greater than 1,024 mg/kg for intraperitoneal administration in mice); in the psychotropic field, it produces the following in the animals:
a sedation, with hypomotility, in mice and rats,
a reduction in the spontaneous motility in mice and a hyper-reactivity in mice and in rats.

6. CRL 40,261 (Example 7) exhibits the following in its psychopharmacological spectrum:
an increase in the duration of the stereotypies brought about by amphetamine in rats,
an increase in the hypothermia due to reserpine (without alteration of the palpebral ptosis induced by reserpine),
a moderate effect towards oxotremorine and
an increase in the spontaneous motility in mice (at doses of 2 mg/kg, 8 mg/kg and 32 mg/kg).

The LD-O of CRL 40,261, administered intraperitoneally in mice, is greater than 256 mg/kg.

7. CRL 40,277 (Example 8) acts on the central nervous system. The following are observed in its psychopharmacological spectrum:
firstly, the following effects at high doses: hypothermia, hypomotility, aggravation of the hypothermic effects of reserpine and oxotremorine, an aggravation of the lethal effects of the electric shock, and
secondly, at medium doses, effects of a type which are more stimulant in nature but are always of very moderate intensity, namely: hyper-reactivity, boosting of the effect of amphetamine and inconstant residual hypermotility.

For intraperitoneal administration to mice, the LD-O of CRL 40,277 is greater than 512 mg/kg.

8. CRL 40,278 (Example 9) acts on the central nervous system. For intraperitoneal administration in mice, its LD-O is greater than 1,024 mg/kg.

I claim:
1. Benzhydrylsulphinyl compounds of the formula:

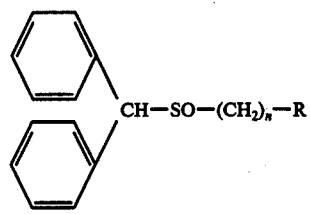

I in which $n$ is 1, 2 or 3 and R is C(=O)NHOH and their addition salts.

2. A compound according to claim 1 which is benzhydrylsulphinyl-acetohydroxamic acid.

3. A compound according to claim 1 which is 3-benzhydrylsulphinyl-propionohydroxamic acid.

4. A compound according to claim 1 which is 4-benzhydrylsulphinyl-butyrohydroxamic acid.

* * * * *